United States Patent [19]
Kalender

[11] Patent Number: 5,235,628
[45] Date of Patent: Aug. 10, 1993

[54] CALIBRATION PHANTOM FOR BONE MINERAL MEASUREMENT ON THE LUMBAR SPINE

[75] Inventor: Willi A. Kalender, Kleinseebach, Fed. Rep. of Germany

[73] Assignee: Wisconsin Alumni Research Foundation, Madison, Wis.

[21] Appl. No.: 797,722

[22] Filed: Nov. 25, 1991

[30] Foreign Application Priority Data

Nov. 26, 1990 [DE] Fed. Rep. of Germany ....... 9016046

[51] Int. Cl.$^5$ ............................................. G01D 18/00
[52] U.S. Cl. ..................................... 378/207; 378/18; 378/56
[58] Field of Search ..................... 378/207, 18, 53, 54, 378/62, 88, 89, 56

[56] References Cited

U.S. PATENT DOCUMENTS

| | | | |
|---|---|---|---|
| 4,126,789 | 11/1978 | Vogl et al. | 378/207 |
| 4,638,502 | 1/1987 | Yaffe | 378/207 |
| 4,646,334 | 2/1987 | Zerhouni | 378/207 |
| 4,870,666 | 9/1989 | Lonn et al. | 378/207 |
| 4,873,707 | 10/1989 | Robertson | 378/207 |
| 4,985,906 | 1/1991 | Arnold | 378/207 |
| 5,122,664 | 6/1992 | Ito et al. | 378/207 |

OTHER PUBLICATIONS

W. A. Kalender, D. Felsenberg, "A Phantom for Standardization and Cross-calibration of Spinal Bone Mineral Measurements by DXA and QCT," Abstract presented at the 8th International Workshop on Bone Densitometry, Bad Reichenhall, Germany, Apr. 28–May 2, 1991, pub. in Osteoporosis Int'l. vol. 1, Jun. 1991, p. 203.

W. A. Kalender, et al., "Cross-calibration Phantom for Spinal Bone Mineral Measurements with Quantitative CT and DXA," Program of the 76th Scientific Assembly and Annual Meeting, Radiological Society of N. America, Chicago, Ill., Nov. 25–30, 1990, 177 (P): p. 306.

W. A. Kalender, et al., "A Cross-Calibration Phantom for Spinal Bone Mineral Measurements In a Multicenter Study," Program of the 1st European Conf. on Biomedical Engineering, Nizza, France, Feb. 19, 1991, pp. 76–77.

Advertisement by CIRS, Computerized Imaging Reference Systems, Inc., for "C. T. Simulator for Bone Mineral Analysis".

Primary Examiner—David P. Porta
Assistant Examiner—Kim-Kwok Chu
Attorney, Agent, or Firm—Foley & Lardner

[57] ABSTRACT

A phantom for use in calibrating dual energy X-ray absorptiometry and quantitative computed-tomography includes one or more sections which are equivalent to bone to X-rays and which have a shape resembling a lumbar vertebra. Each section includes a substantially cylindrical main body simulating the vertebra centrum, a band simulating the neural arch, and transverse and posterior processes extending from the band. The transverse processes are formed in a define wedge shape which tapers down from its attachment to the neural arch band. The section, or stacked sections, are embedded in a matrix of plastic material equivalent to water or tissue.

14 Claims, 6 Drawing Sheets

CALIBRATION PHANTOM FOR BONE MINERAL MEASUREMENT ON THE LUMBAR SPINE

BACKGROUND OF THE INVENTION

Osteoporosis, a severe aging disease of the skeleton, gains ever growing importance due to the continuously increasing life expectancy. The annual cost to the health care system due to osteoporosis is estimated to amount up to several billions worldwide, in Germany one estimate is about 1 billion. Clinical and measurement efforts for an early diagnosis and efficient control of therapy are accordingly high.

Two procedures have shown to be particularly suitable for bone mineral measurements:

Photon absorptiometry (DXA, Dual Energy X-ray Absorptiometry) and quantitative computed tomography (QCT). For each modality there are more than 1000 installations of various manufacturers in use worldwide.

A particular problem and serious controversies have evolved from the fact that results which have been obtained on different units do not agree or can hardly be compared, respectively. In particular, for the DXA scanners, each manufacturer uses different phantoms both for calibration and for quality control. Due to the fact that different materials and different geometries are employed, calibrations are different Differences result for measurements of the same object or patient on different apparati. The phantoms available mostly offer homogeneous bone without separation of spongious and cortical portions. Due to their anthropomorphic shape, it is not possible to determine if the presented area values and the directly resulting area density values are correct.

In QCT, the manufacturers do not offer anthropomorphic phantoms. There are only some smaller specialized companies which offer such phantoms. These are not useful for direct comparison to DXA; also, they do not offer defined cortical structures. Since so far only solutions specific to one manufacturer and one scanner type have been offered, controversies resulted, but no accepted solution to the problem of cross-calibration of different devices. In addition, it has to be stated that the phantoms offered by small specialized companies are very expensive, partly not very practical and they do not offer all the desired test procedures.

It appears desirable to have only one phantom to simulate bone mineral measurements of the lumbar spine with both absorptiometry and QCT. It will help to reduce cost to have only one phantom instead of two different ones in those institutions who use both modalities. More important, however, is the intent to avoid a diversity of different phantom geometries and materials. This would be counterproductive in any standardization effort, and it might reinforce confusion or irritations in the user community.

For DXA, both a.p. and lateral measurement capabilities have to be provided. For QCT, separate measurement of spongious and cortical bone is required. The phantom should allow testing of reproducibility and accuracy of machines, both in clinical installations and at manufacturers' sites, in determining the following quantities:

projected area of vertebrae in $cm^2$ for DXA,
bone mineral content (BMC) in g for DXA,
trabecular and cortical bone mineral density in $g/cm^3$ for QCT,
cortical thickness in mm for QCT,
positioning in QCT.

Bone mineral area density (BMD) in $g/cm^2$, which is the quantity most often quoted in DXA, results directly from the above. Tests of linearity have to be provided also and require that the phantom offers either multiple sections or multiple inserts. The respective sections of inserts should cover the range of density values typically encountered in patients.

To perform appropriately, two general demands on the phantom must be met:

for all of the above measurements, the true values have to be known and defined in an objective manner;

the phantom has to be designed in a way such that results of phantom measurements model the situation of patient measurements appropriately.

The first demand is absolutely necessary for the phantom to be used as a standard. The second demand is a logical one if the phantom is to give relevant results; in a particular, this means that cross-calibration factors obtained on the phantom have to be transferable to patient measurements.

SUMMARY OF THE INVENTION

The present invention has the aim to provide a phantom, which can be employed in both DXA and QCT, for calibration and quality control of devices for bone mineral measurements of the lumbar spine. The use of only one phantom with clearly defined, closely anthropomorphic geometry and standard materials facilitates standardization and eliminates the partly unnecessary controversies.

The defined task has been solved in the present invention by designing a body from soft tissue and water-equivalent materials which resembles a vertebra. The phantom also consists of tissue and water-equivalent materials, respectively; for this purpose epoxy resins are used as a basis material, with different chemicals of different concentrations to be added, to receive solids which are equivalent to water, soft tissue and bone tissue with respect to their attenuation characteristics for X-rays. The total phantom in a typical implementation has an oval cross section of 18 cm×28 cm and a depth of approximately 12 cm. Additions (e.g. rings or plates) made of water or fat-equivalent materials can be added. The sides can be flattened to allow for stable lateral positioning. In this form the phantom can be easily handled with respect to size and mass (<5 kg). It can basically consist of three sections which contain a vertebra of different dimensions and mineral densities each.

Due to the exact geometrical definition of all structures, still keeping a close approximation to anthropomorphic shape, all quantities can be calculated and, when manufactured correctly, true values of the measured quantities can be specified.

With DXA, both a.p. and lateral measurements are possible. Area ($cm^2$), area densities ($g/cm^2$), mass (g), and linearity of measurements can be checked.

For QCT, both spongious and cortical density can be measured and linearity can be checked. In addition, a drill hole in the central section gives the possibility to check the positioning accuracy of the device.

Further objects, features and advantages of the invention will be apparent from the following detailed description when taken in conjunction with the accompanying drawings.

DETAILED DESCRIPTION OF THE INVENTION

Figure 1:
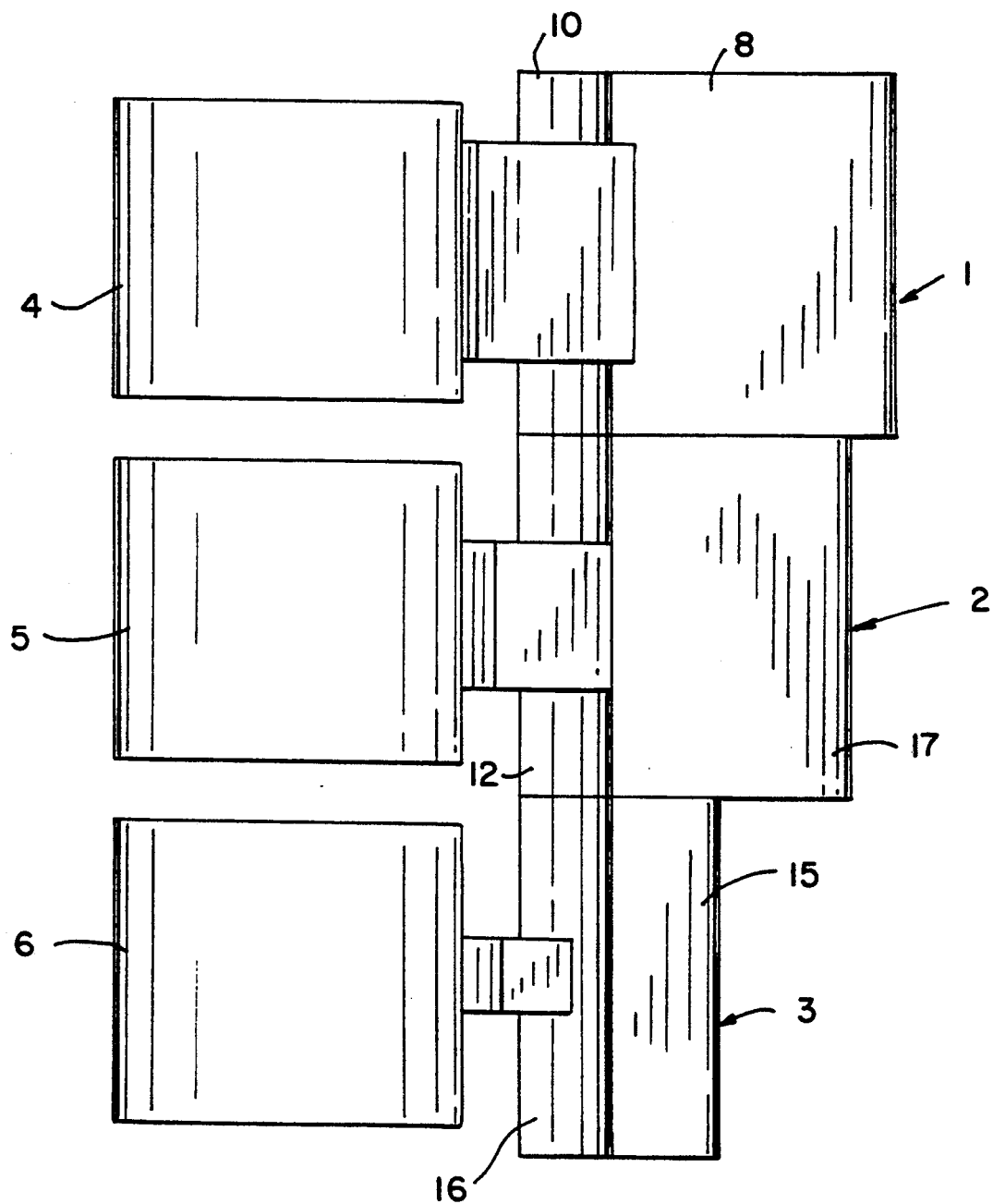
FIG. 1 is a lateral projection of the 'bony structures' of the phantom of the invention with three sections according to the invention.

The phantom in FIG. 1 consists of three sections 1 to 3 each has a basic body 4, 5, and 6, respectively, made of tissue and water-equivalent materials which mimic a vertebra. To the basic body 4, 5, and 6 additional bodies 7 to 18 made of tissue and water-equivalent materials are attached to better approximate an anthropomorphic shape.

The components 4, and 7-10; 5, and 11-14; 6, and 15-18 have different dimensions and densities to mimic vertebrae of different dimensions.

A specific form of the phantom which would be produced for the sole use in QCT, consists of the central section, e.g. with a depth of 3 cm. For this version the spongiosa insert can be exchanged. Inserts of different mineral densities and fat content can be supplied.

The bodies 4, 5 and 6 of the sections 1, 2 and 3, respectively, are each substantially cylindrical in shape to simulate the centrum of a vertebra; and each has a cortical wall which surrounds an open bore into which material equivalent to spongious bone can be inserted. Semicircular bands 10, 12 and 16 are attached to the bodies 4, 5 and 6, respectively, to simulate the neural (vertebral) arch. Transverse process structures 7 and 9, 13 and 14, and 17 and 18 extend from the neural arch bands 10, 12 and 16, respectively, as do posterior process structures 8, 11 and 15.

To avoid controversy with respect to the definition of different tissue substitute materials, the phantom constituents may be limited to water- and bone-equivalent solid materials. For such purposes, polyethylene-based (see V. Faust et al., Biomed Tech. 1986, 31:175-177; W. A. Kalender et al., Radiology 1977, 164:419-423; W. A. Kalender et al., Med. Phys. 1987, 14:863-866) and epoxy-resin-based plastics are in use (see D. R. White, et al., British J. Radiology 1977, 50:814-821). polyethylene plastics are attractive for large-volume production because industrial processes are required; cross-sections should be limited to a few cm only to achieve adequate homogeneity. Epoxy resins offer the advantage that they can be molded in arbitrary shapes and cross-sections, but they demand manual labor and only limited quantities of less than 5 kg can be processed at a time. Epoxy-resin-based materials are preferred initially because they are more easily adopted to arbitrary design specifications.

Water-equivalent materials are here defined as plastics which exhibit the same attenuation characteristics as water with respect to X-rays in the energy range of 30 keV to 150 keV. Such plastics have been developed following the basic prescriptions of White et al., supra. In addition to the epoxy-resin system, $CaCO_3$ has been added to adjust the effective atomic number and phenolic microspheres have been added to adjust the density of the material. In addition, polyethylene contributions have been used to control the viscosity of the final mixture; this is of particular importance if hydroxyapatite is added. An exemplary preferred composition for water equivalent material is 77.52% epoxy resin, 3.50% microspheres, 3.98% $CaCO_3$, and 15.00% polyethylene. Bone-equivalent tissues ar provided by adding calcium hydroxyapatite (HA) to the water-equivalent mixture. A range of 0-800 mg HA/$cm^3$ can be provided.

Figure 8:
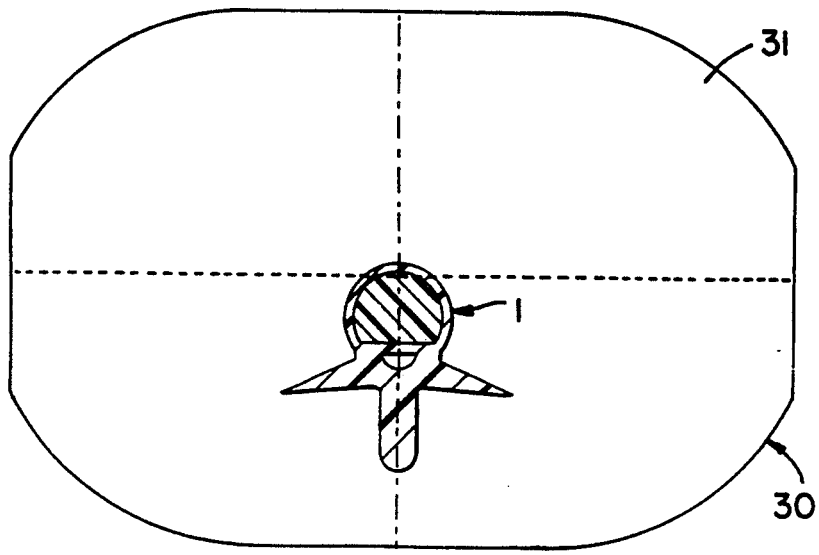
FIGS. 8-10 are illustrative views of each of the vertebra sections shown in exemplary positions for CT scans.
Figure 9:
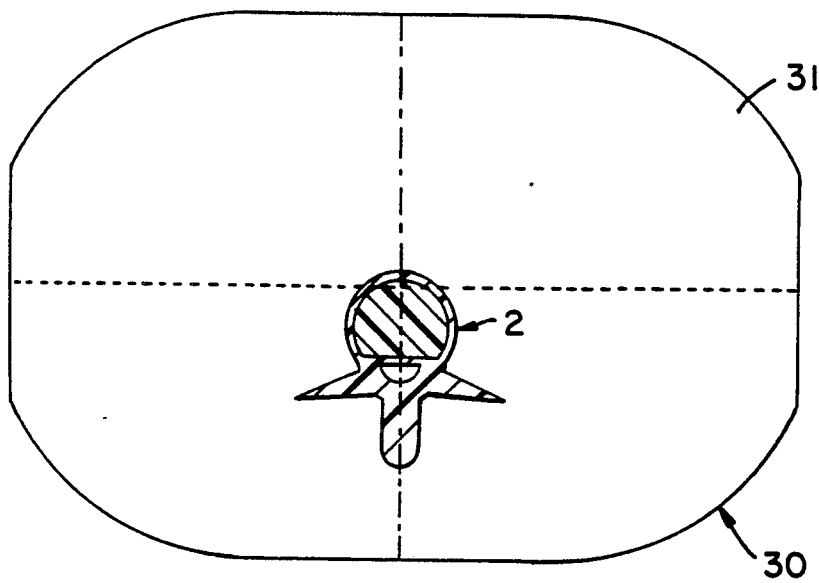
Figure 10:
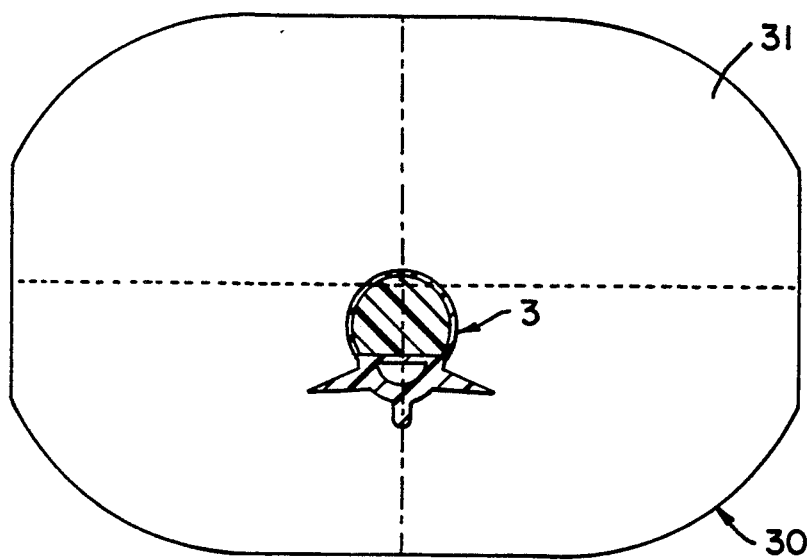
Figure 11:
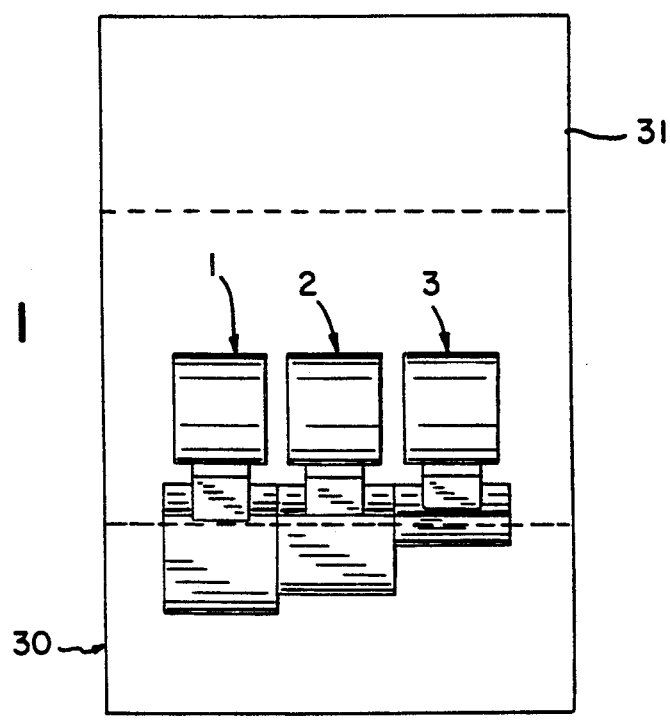
FIGS. 11 and 12 are side views of the phantom of FIG. 1 positioned for a CT scan.
Figure 12:
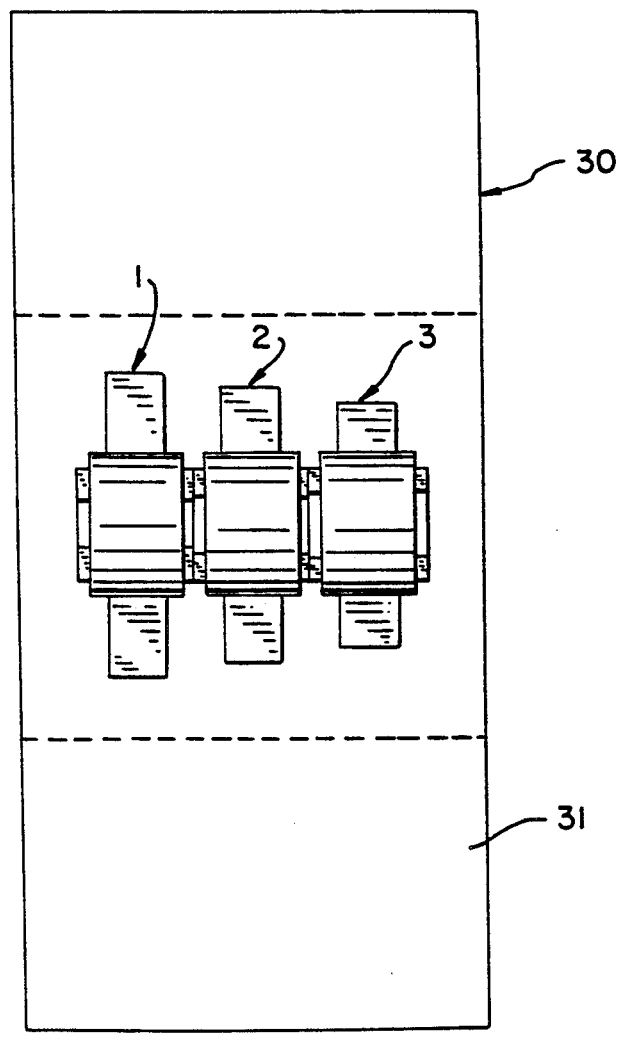

As noted above, the phantom is preferably composed of three sections 1, 2 and 3 each defining a simulated vertebra of different bone mineral content and area density. This is achieved by varying the HA concentrations in spongious and cortical bone equivalent material. The basic geometry and density parameters are summarized in table 1 below and illustrated in FIGS. 8-10. Some parameters, like spongious HA densities, cortical HA densities and cortical wall thicknesses, have been fixed based on accepted values in the literature. A range of spongious HA densities from 50-200 mg HA/$cm^3$ appears appropriate. See C. E. Cann, et al., Bone 1985, 6:1-7; W. A. Kalender, et al., Europ. J. Radiology 1989, 9:75-80. Cortical wall thicknesses of 1, 2 and 3 mm for the three sections 1, 2 and 3 were selected on the basis of CT measurements. For cortical densities, few reliable data are available, as a mixture of cortical and spongious structures is mostly given due to the limited spatial resolution of the available imaging modalities. An average of about 400 mg HA/$cm^3$ was evaluated for the vertebral cortical walls as well as for the appendicular structures. A constant density of 400 mg HA/$cm^3$ was chosen for all vertebral body cortical walls to be able to test the influence of spatial resolution of existing systems on results. Other parameters, like lengths and thicknesses of the spinous (posterior) processes, were determined by computer calculations to arrive at the desired BMC and, consequently, BMD values in a.p. projection of 0.5, 1.0 and 1.5 g/$cm^2$, respectively. The bone mass of the vertebral body was intended to be approximately the same as the bone mass of the arch and the posterior and the transverse processes (see BMC values for a.p. and lateral projection in Table 1).

TABLE 1

Design Parameters of the Vertebral Inserts

| Parameters | Vertebra | | |
|---|---|---|---|
| | Low | Medium | High |
| Geometry (values in mm) | | | |
| body diameter | 36 | 36 | 36 |
| arch diameter | 28 | 28 | 28 |
| height | 25 | 25 | 25 |
| body wall thickness | 1 | 2 | 3 |
| endplate thickness | 1 | 1 | 1 |
| arch thickness | 5.7 | 7 | 8 |
| spinous process thickness | 6 | 12 | 12 |
| spinous process length | 8.5 | 21.6 | 27.5 |
| Densities (values in mg hydroxyapatite/$cm^3$) | | | |
| spongiosa | 50 | 100 | 200 |
| walls and endplates | 400 | 400 | 400 |
| arch and processes | 300 | 400 | 500 |
| A.p. projection of vertebral body | | | |
| area, $mm^2$ | 900 | 900 | 900 |
| BMC, g | 4.5 | 9.0 | 13.5 |
| BMD, g/$cm^2$ | 0.5 | 1.0 | 1.5 |
| Lateral projection of vertebral body | | | |
| area, $mm^2$ | 732.8 | 732.8 | 732.8 |
| BMC, g | 2.58 | 4.17 | 6.16 |
| BMD, g/$cm^2$ | 0.35 | 0.57 | 0.84 |

Figure 2:
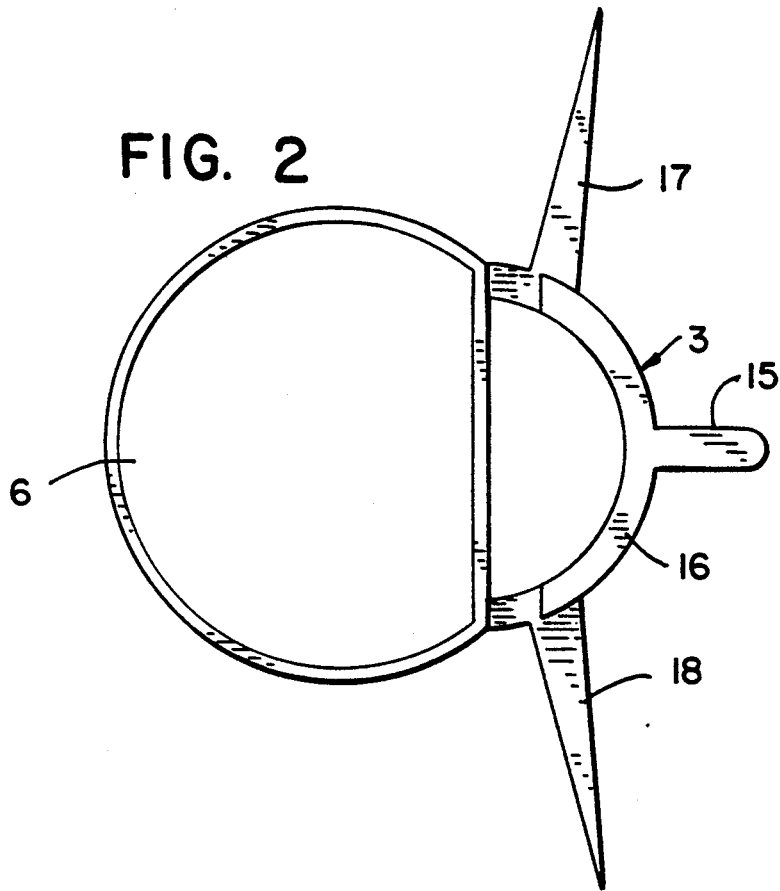
FIGS. 2-7 are top and side views of each of the vertebra sections according to FIG. 1.
Figure 3:
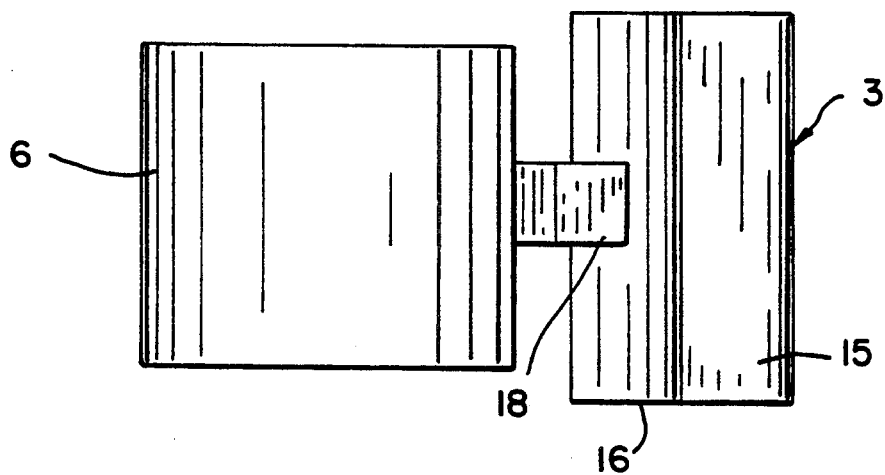
Figure 5:
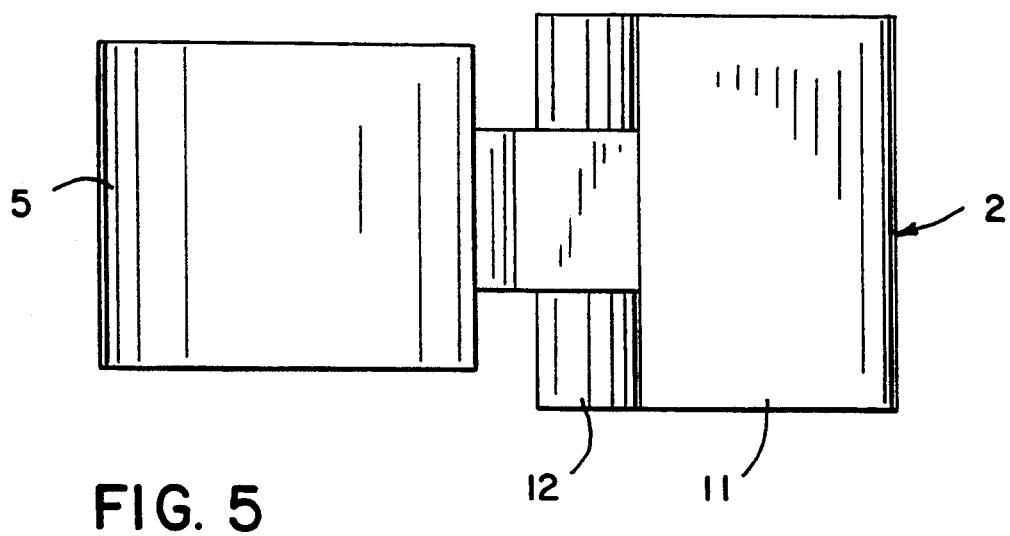
Figure 4:
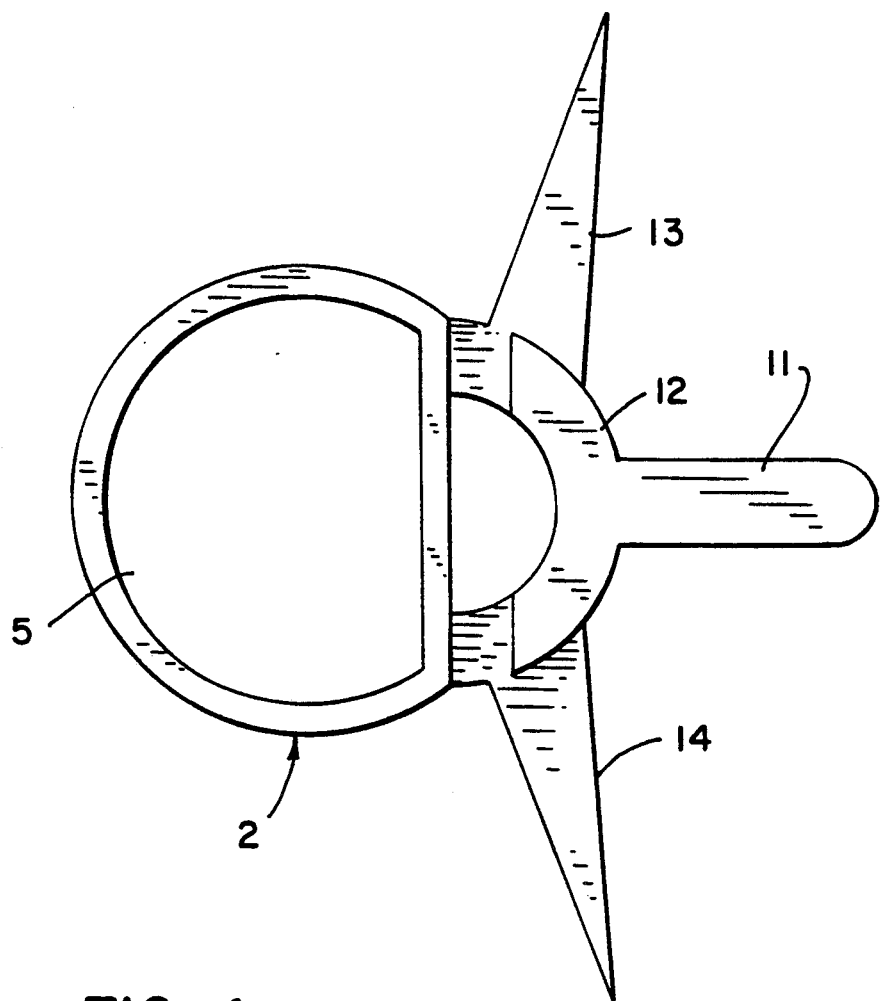
Figure 6:
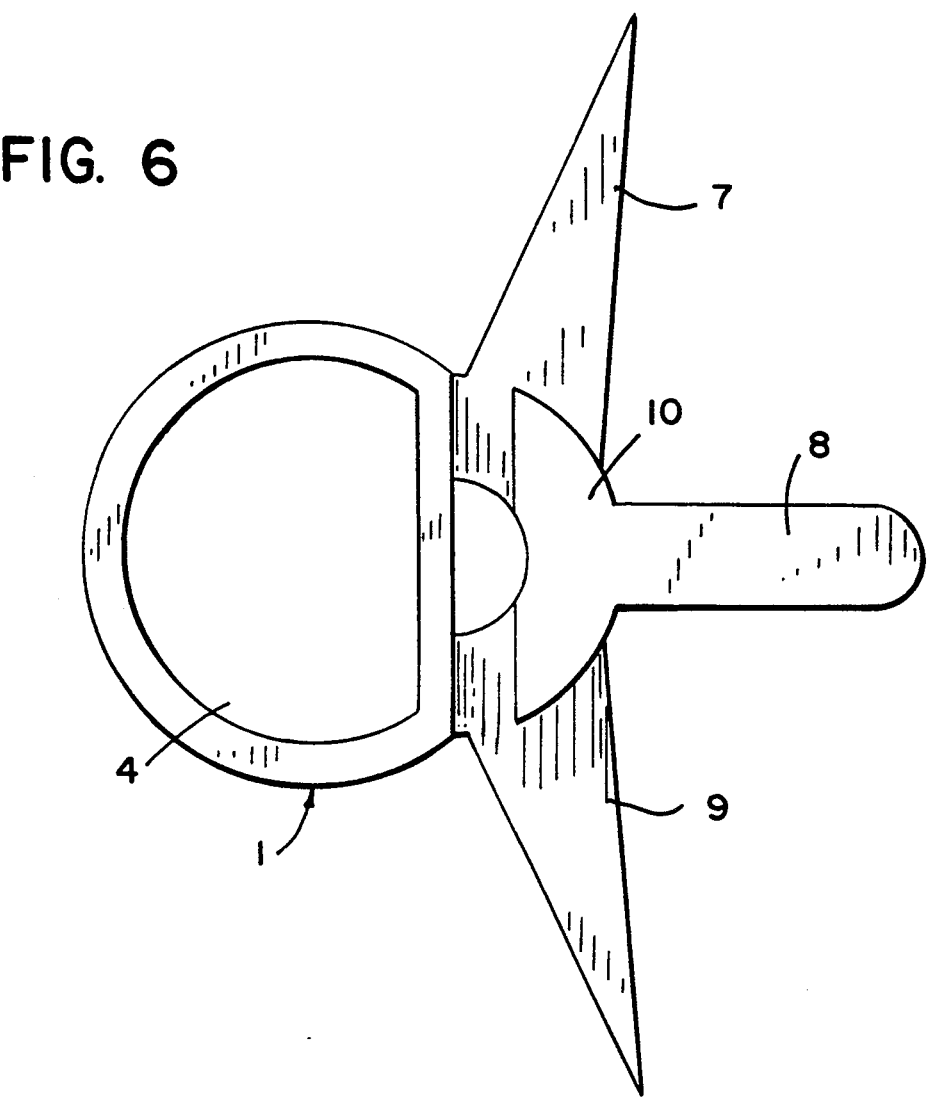
Figure 7:
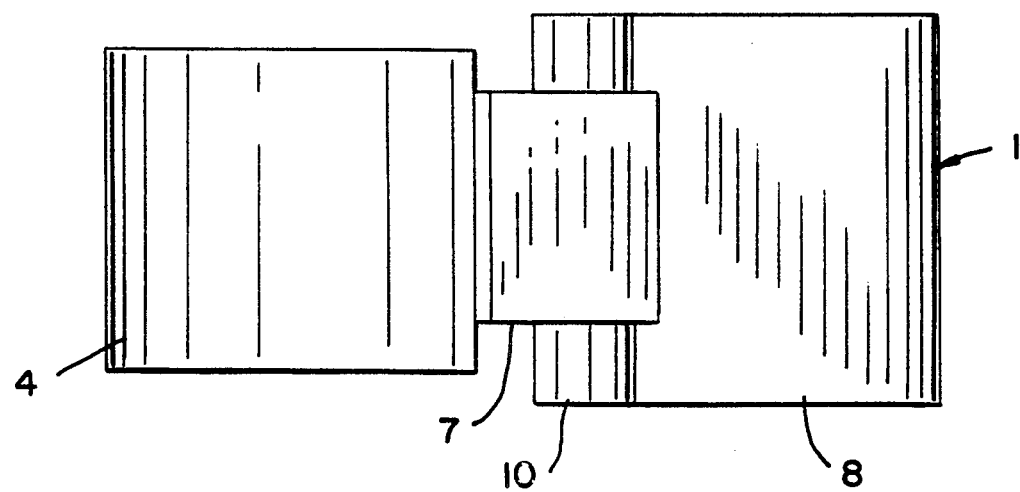

The geometric design of the transverse processes 7, 9, 13, 14, 17 and 18 as ramps (see FIGS. 2, 4 and 6) is intended to test the cutoff criteria employed in different DXA apparatus as they are essential in area determination. The dimensions of the vertebral bodies were chosen with 36 mm in width and 25 mm in height. Intervertebral spaces were set at 5 mm.

A complete oval phantom 30 cross-section of 18 cm×28 cm, as illustrated in FIGS. 8-12, was chosen; with the sides of the phantom 30 flattened by 1 cm to allow for easy lateral positioning, a lateral diameter of 26 cm results. The completed phantom 30 is produced by positioning the simulated vertebrae 1, 2 and 3 in a mold and then filling the mold with water equivalent epoxy resin which forms a matrix 31 in which the vertebrae 1, 2 and 3 are embedded. The a.p. thickness of 18 cm of solid water appears realistic to approximate attenuation by the mean 20 cm a.p. thickness found in humans (See H. Vogel, Ecomed. Verlag, Landsberg 1989) which includes fat and/or abdominal gas. A lateral thickness of 26 cm of solid water is known and recommended as typical for lateral measurements in the decubitus position. To simulate greater thicknesses in both directions, plates of water-equivalent materials can easily be added as all sides are flat. A hole of 1.5 mm diameter and 10 mm depth drilled laterally in the phantom serves as a positioning test for CT. The preferred positioning of the vertebrae in the matrix 31 is illustrated in FIGS. 8-12.

Manufacturing tolerances may be set as follows:
geometric measures: $+/-0.1\%$ (at best 0.1 mm)
hydroxyapatite concentrations: $=/-0.2\%$ (at best 0.2 mg/cm$^3$)
homogeneity of materials: $+/-5$ HU standard deviation
CT value of solid water: $+/-10$ HU (in reference to distilled water)

Routine quality control on phantom production should be carried out by CT. It is the method of choice to test homogeneity of the materials, but it is also appropriate for all other parameters. The phantoms have to be scanned contiguously to check for homogeneity and any possible manufacturing defects. In addition, a standard QCT study of the 3 midvertebral slices has to be carried out. DXA measurements are also used to check and document consistency of production.

The need for standardization in bone mineral measurements has been recognized for quite some time. Respective efforts have been demanded or initiated on national and international levels by AAPM, COMAC-BME, EOF, NOF and other organizations.

It has to be acknowledged that the phantom design of the invention only approximates an anthropomorphic shape in a crude way; the relevant properties, however, are simulated appropriately. A distinct advantage of the geometric design of the invention is that true values of all parameters to be measured can be specified exactly. In particular, this applies to area definitions which constitute a problem in DXA. Most users of DXA acknowledge that some parts of the transverse processes are included if they are strongly mineralized; the amount depends on the threshold or contour finding algorithm employed. The intervertebral space is mostly included, but does not have to be a priori. Whatever the criteria shall be, true area value for the phantom can be specified in any case to thereby offer a test and a standard.

The interest in cortical measurements by QCT has been enhanced lately by reports on different loss rates in cortical and spongious bone. Such measurements can only be performed by CT; so far, however, no adequate tools have been provided to test their accuracy. The phantom of the invention offers such means with respect to the density and thickness of the cortical walls of the vertebral body. The simple, but accurate positioning test incorporated into the phantom might also prove valuable.

It is understood that the invention is not confined to the particular embodiments set forth herein as illustrative, but embraces such modified forms thereof as come within the scope of the following claims.

What is claimed is:

1. A phantom, adapted for calibration of devices for the measurement of bone mineral content by X-rays, which mimics a vertebra comprising:
    (a) a main body having a substantially cylindrical shape simulating a centrum of a vertebra and having a cortical wall formed of a material equivalent to bone to X-rays;
    (b) a semicircular band of material attached to the main body simulating the neural arch of a vertebra and formed of a material equivalent to bone to X-rays;
    (c) transverse processes extending outwardly from the semiconductor band simulating the neural arch, the transverse processes formed in a wedge shape which tapers down from its attachment to the neural arch band, the transverse processes formed of a material equivalent to bone to X-rays.

2. The vertebra phantom of claim 1 wherein the material forming the vertebra phantom includes a plastic material which exhibits the same X-ray attenuation characteristics as water.

3. The vertebra phantom of claim 2 wherein the plastic forming the phantom has calcium hydroxyapatite added thereto to provide a bone equivalent structure.

4. The vertebra phantom of claim 1 wherein the centrum of the main body has a central portion formed of a material having lower bone equivalent density than the cortical wall of the main body.

5. The vertebra phantom of claim 1 including a matrix surrounding the vertebra, the matrix including a plastic material which exhibits the same X-ray attenuation characteristics as water.

6. The vertebra phantom of claim 1 including a posterior process formed of a material equivalent to bone to X-rays extending from the band simulating the neural arch.

7. A phantom, adapted for calibration of devices for the measurement of bone mineral content by X-rays, which mimics a portion of the vertebra of the lumbar spine to X-rays comprising:
    a plurality of vertebra simulating sections in stacked relation, each section, including:
    (a) a main body having a substantially cylindrical shape simulating a centrum of a vertebra and having a cortical wall formed of a material equivalent to bone to X-rays;
    (b) a semicircular band of material attached to the main body simulating the neural arch of a vertebra and formed of a material equivalent to bone to X-rays;
    (c) transverse processes extending outwardly from the semicircular band simulating the neural arch, the transverse processes formed in a wedge shape which tapers down from its attachment to the neural arch band, the transverse processes formed of a material equivalent to bone to X-rays.

8. The phantom of claim 7 wherein the material forming the vertebra of the phantom includes a plastic which exhibits the same X-ray attenuation characteristics as water.

9. The phantom of claim 8 wherein the plastic forming the phantom has calcium hydroxyapatite added thereto to provide a bone equivalent structure.

10. The phantom of claim 7 wherein the centrum of the main body of each vertebra has a central portion formed of a material having lower bone equivalent density than the cortical wall of the main body.

11. The phantom of claim 7 wherein the simulated transverse and posterior processes of each vertebra are of a different height and length.

12. The phantom of claim 7 wherein the phantom has three sections.

13. The phantom of claim 7 including a matrix surrounding the stacked vertebrae, the matrix including a plastic material which exhibits the same X-ray attenuation characteristics as water.

14. The phantom of claim 7 including a posterior process formed of a material equivalent to bone to X-rays extending from the band simulating the neural arch.

* * * * *

UNITED STATES PATENT AND TRADEMARK OFFICE
CERTIFICATE OF CORRECTION

PATENT NO. : 5,235,628
DATED : August 10, 1993
INVENTOR(S) : Willi A. Kalender

It is certified that error appears in the above-indentified patent and that said Letters Patent is hereby corrected as shown below:

In column 1, line 28 of the patent, "different Differences" should be --different. Differences-- as written in the application on page 2, line 1.

In column 4, line 7 of the patent, "tissues ar" should be --tissues are-- as written in the application on page 6 line 36.

In column 6, line 26 of the patent, "semiconductor" should be --semicircular-- as per amendment dated November 27, 1992.

Signed and Sealed this

Fifth Day of April, 1994

*Attest:*

BRUCE LEHMAN

*Attesting Officer*   *Commissioner of Patents and Trademarks*